Nov. 20, 1962 E. S. BOERNER Plant Pat. 2,196
ROSE PLANT
Filed Jan. 17, 1962
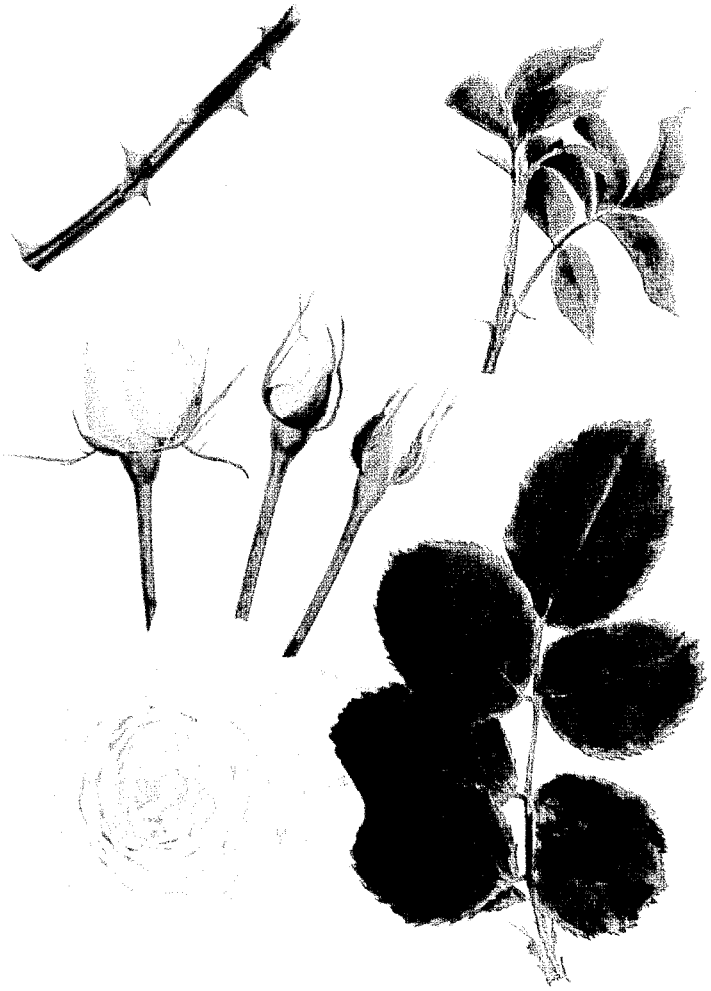
Inventor.
E. S. Boerner
By: Robb & Robb
Attorneys.

United States Patent Office

Plant Pat. 2,196
Patented Nov. 20, 1962

2,196
ROSE PLANT

Eugene S. Boerner, Newark, N.Y., assignor to Jackson & Perkins Company, Newark, N.Y., a corporation of New York Filed Jan. 17, 1962, Ser. No. 166,973
1 Claim. (Cl. 47—61)

The present invention relates to a new and distinct variety of rose plant of the floribunda class, which was originated by me by crossing the variety "Queen Elizabeth" (Plant Patent No. 1,259) with the variety "Spartan" (Plant Patent No. 1,357).

The primary objective of this breeding was to produce a new rose variety characterized by a medium tall habit of growth, combined with pink flowers preferably of a color comparable to the color of the flowers of the parent variety "Queen Elizabeth." This objective was fully achieved, along with other desirable features, as evidenced by the following unique combination of characteristics which are outstanding in the new variety and which distinguish it from its parents, as well as from all other varieties of which I am aware:

(1) A clean, upright, and medium tall habit of growth (not as tall as "Queen Elizabeth");

(2) Rich fragrance of the flowers; and (3) A distinctive and attractive pink general color tonality of the flowers corresponding to Thulite Pink, lightly overcast with La France Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Queen Elizabeth."
*Pollen parent.*—"Spartan."
Classification:
*Botanic.*—Floribunda.
*Commercial.*—Floribunda.

*Flower*

(Observations made from specimens grown outdoors at Newark, New York, in the early morning during the latter part of the month of August.)

Blooming habit: Recurrent—continuous.
Bud:
*Size.*—Large.
*Form.*—Ovoid; is not affected by wet or hot weather.
*Color.*—When sepals first divide—Rose Red, Plate 12. When petals begin to unfurl—Scarlet Red, Plate 1, very lightly overcast with Rose Doree, Plate 1. When half-blown: inside of petals—Eosine Pink, Plate 1; reverse of petals—Begonia Rose, Plate 1, lightly overcast with Eosine Pink, Plate 1.
*Sepals.*—Slightly serrated; curl back when petals begin to unfurl. Color: inside—Absinthe Green, Plate 31; outside—Deep Dull Yellow Green (1), Plate 32.

*Calyx.* — Color — Chromium Green, Plate 32. Shape — funnel. Size — long. Aspect — smooth. Odor when rubbed—none.
*Peduncle.* — Length — medium. Aspect — smooth. Strength — erect; heavy. Color — Cerro Green, Plate 5.
*Opening.*—Opens up well; is not affected by adverse weather conditions.
Bloom:
*Size.*—Large. Average size when fully expanded—4½ inches.
*Borne.*—Several together and in clusters.
*Stems.*—Medium length; strong.
*Form (when first open).*—Cupped. Permanence—retains its form to the end.
*Petalage.*—Double (full but open center). Number of petals under normal conditions—from 35 to 40.
*Color.*—Center of flower—Begonia Rose, Plate 1, very lightly overcast with Rose Red, Plate 12. Outer petals—La France Pink, Plate 1. Base of petals (aiglet)—Sulphur Yellow, Plate 5. Inside of petals—Thulite Pink, Plate 26, lightly overcast with La France Pink, Plate. 1. Reverse of petals—Hermosa Pink, Plate 1, very lightly overcast with La France Pink, Plate 1. General tonality from a distance—Thulite Pink, Plate 26, lightly overcast with La France Pink, Plate 1.
*Discoloration.*—General tonality at end of first day—Thulite Pink, Plate 26, lightly overcast with La France Pink, Plate 1. Second day—Thulite Pink, Plate 26, lightly overcast with La France Pink Plate 1. Third day—La France Pink, Plate 1.
Petals:
*Texture.*—Thick; is not affected by wet or hot weather.
*Appearance.*—Inside—shiny. Outside—satiny.
*Form.*—Oval.
*Arrangement.*—Imbricated (regularly arranged shingle-like).
*Petaloids in center.*—Many; small.
*Persistence.*—Drop off cleanly.
*Fragrance.*—Strong. Nature—tea (average hybrid tea scent); very sweet.
*Lasting quality.*—On the plant—long. As cut flower—long.

*Genital Organs*

Stamens, anthers: Medium size; many; regularly arranged around styles. Color—Light Orange-Yellow, Plate 3.
Stamens, filaments (threads): Medium length. Color—Maize-Yellow, Plate 4.
Pollen: Color—Pale Yellow-Orange, Plate 3.
Styles: Bunched; uneven length; medium length; thin.
Stigmas: Color—Pinard Yellow, Plate 4.
Ovaries: All enclosed in calyx.
Hips: None.
Seeds: None.

*Plant*

Form: Bush.
Growth: Vigorous; upright; 2½ feet tall.
Foliage: Compound of 3–7 leaflets.
*Size.*—Medium.
*Quantity.*—Normal.
*Color.*—New foliage: upper side—Oil Green, Plate 5, with serrations of Acajou Red, Plate 13; under side—Biscay Green, Plate 17, lightly overcast with Pompeian Red, Plate 13. Old foliage: upper side—Forest Green, Plate 17; under side—Light Bice Green, Plate 17.
*Shape.*—Oval pointed.
*Texture.* — Upper side — glossy. Under side—smooth.

*Ribs and veins.*—Ordinary.
*Edge.*—Serrated (saw toothed).
*Serration.*—Both double and single; small.
*Leaf stem.*—Color—Kronberg's Green, Plate 31. Under side—smooth.
*Stipules.*—Medium length; smooth.

Wood:

*New wood.*—Color—Rinnemann's Green, Plate 18. Bark—smooth.
*Old wood.*—Color—Empire Green, Plate 32. Bark—smooth.

Thorns:

*Thorns.*—Quantity: on main stalks from base—ordinary; on laterals from stalk — ordinary. Form—narrow base; medium length; hooked downward. Color (when young)—Eugenia Red, Plate 13. Position—irregular.

*Prickles.*—Quantity: on main stalks—none; on laterals—none.
*Short needles.*—Quantity: on main stalks—none; on laterals—none.

I claim:

A new and distinct variety of rose plant of the floribunda class, substantially as herein shown and described, characterized particularly as to novelty by the unique combination of a clean, medium tall and upright habit of growth, rich flower fragrance, and a distinctive and attractive pink general tonality of the flowers corresponding to Thulite Pink, lightly overcast with La France Pink.

No references cited.